(12) United States Patent
Gorsek

(10) Patent No.: US 6,649,195 B1
(45) Date of Patent: *Nov. 18, 2003

(54) EYESIGHT ENHANCED MAINTENANCE COMPOSITION

(75) Inventor: Wayne F. Gorsek, Boynton Beach, FL (US)

(73) Assignee: Vitacost.com, Inc., Boynton Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/192,558

(22) Filed: Jul. 11, 2002

(51) Int. Cl.[7] ............................................... A61K 35/78
(52) U.S. Cl. ...................... 424/732; 424/752; 424/766; 514/912; 514/913
(58) Field of Search ................................ 424/732, 752, 424/766; 514/912, 913

(56) References Cited

U.S. PATENT DOCUMENTS

| | | | |
|---|---|---|---|
| 5,804,597 A | * | 9/1998 | Yamakoshi et al. |
| 5,955,102 A | * | 9/1999 | Gorenbein et al. |
| 6,103,756 A | * | 8/2000 | Gorsek |
| 6,207,190 B1 | * | 3/2001 | Richardson et al. |

OTHER PUBLICATIONS

Product Alert (May 1996), pp N/A. Quantum Herbal See Nutrients for Your Eyes–Liquid Supplement; Manufacturer: Quantum, Inc.; Category: Vitamins & Tonics.*

Lookout (Non Foods Edition), (Feb. 1998), pp N/A. Celestial Seasonings total antioxidant dietary supplement. Is marketing its Total Antioxidant Dietary Supplement under the firm's Celestial Seasonings tea brand name. Abstract.*

Product Alert (Nov. 1998), pp N/A. Interact Supplement–Original Tablets; Mood Tablets; Eye Tablets Manufacturer: Alacer Corp.; Category: 363–Vitamins & Tonics.*

Japanscan Food Industry Bulletin (Jan. 2000), pp 21. Japan: Supplement to Relieve Eyestrain. Abstract.*

* cited by examiner

Primary Examiner—Christopher R. Tate
Assistant Examiner—Michele C. Flood
(74) Attorney, Agent, or Firm—Hoffman, Wasson & Gitler, P.C.

(57) ABSTRACT

A powerful formulation for preventing and treating macular degeneration, cataracts, glaucoma and other eye diseases, and contains over thirty naturally effective vitamins, minerals, phytonutrients and amino acids, which have all been found to demonstrate a powerful protective effect on the health of the eye.

2 Claims, No Drawings

EYESIGHT ENHANCED MAINTENANCE COMPOSITION

BACKGROUND OF THE INVENTION

The invention relates to a composition for maintaining healthy eyesight. The composition provides over thirty naturally effective vitamins, minerals, phytonutrients and amino acids, which have all been found to demonstrate a powerful protective effect on the health of the eye.

Vision loss is often related to damage caused by free radicals. A free radical is a highly reactive molecule that binds to and destroys body components. Free radicals are found in every thing from air pollution and chemicals in the water we drink, to preservatives in the foods we eat and cigarette smoke.

As a result of their dependence on light to function properly, the eyes are especially vulnerable to free radical attacks. Paradoxically, while this light enables a person to see, it also creates additional free radicals that lead to cell and membrane damage.

Applicant has discovered that certain nutrients and antioxidants can help neutralize dangerous free radicals, and may even provide additional benefits for maintaining healthy vision. These specific nutrients, in a specific formulation form the basis of the vision maintenance formulation, embodying the invention.

It is an object of the present invention to provide a unique formulation which allows individuals to maintain good eyesight and prevent debilitating degeneration which can lead to blindness.

SUMMARY OF THE INVENTION

The key to the unique formulation is a combination of effective amounts of specific vitamins, minerals, phytonutrients and amino acids. These essential components protect and neutralize free radicals that damage vision and the body.

The formulation contains: natural carotenoids: beta carotene, alpha carotene, lutein, zeaxanthin, cryptoxanthin and palmitate(Vitamin A); magnesium ascorbate (Vitamin C); d-alpha tocopherol, gamma tocopherol, delta tocopherol and beta tocopherol(Vitamin E); Alpha Lipoic Acid; Bilberry Extract; L-Taurine(a amino acid from magnesium taurinate); Lutein Extract which contains zeaxanthin and lutein; Docosahexaenoic Acid (DHA—omega-3 fatty acid); Ginkgo Biloba; and Grape Seed Extract.

The formulation is preferably delivered in capsule, tablet and/or softgel form.

DETAILED DESCRIPTION OF THE INVENTION

The present invention involves a composition for oral ingestion that contains an effective amount of natural carotenoids: beta carotene, alpha carotene, lutein, zeaxanthin, cryptoxanthin and palmitate(Vitamin A); magnesium ascorbate (Vitamin C); d-alpha tocopherol, gamma tocopherol, delta tocopherol and beta tocopherol(Vitamin E); Alpha Lipoic Acid; Bilberry Extract; L-Taurine(a amino acid from magnesium taurinate); Lutein Extract which contains zeaxanthin and lutein; Docosahexaenoic Acid (DHA—omega-3 fatty acid); Ginkgo Biloba; and Grape Seed Extract and other minor nutrients. More specifically, this formulated product is highly effective at maintaining healthy eyesight. This product also stabilizes, treats, reverses and prevents age related macular degeneration (ARMD), glaucoma, cataracts, diabetic retinopathy and other eye diseases. The formula will treat, stabilize, reverse and prevent heart disease, atherosclerosis, myocardial infarctions (heart attacks), artery stenosis and stroke.

In order to secure the desired result the following essential components are provided:

Carotenoids (lutein and zeaxanthin found in spinach and lycopene found in tomatoes) help to protect the retina from oxidative damage initiated in part by absorption of light 20 mg lutein and zeaxanthin 880 mcg (100 mcg–1,000 mg of each);

Vitamins C (1,000 mg)(10 mg–15,000 mg) and E (500IU) (50IU–5,000IU) have demonstrated a significant protective effect against light-induced damage;

Vitamin A is essential for night and color vision (5,000 IU)(1,750IU–175,000IU);

Alpha Lipoic Acid is one of the most powerful antioxidants ever discovered. It is the only antioxidant that protects both the water and lipid parts of the cell. It reduces free radicals and oxidative stress in the lens of the eye and the body (300 mg)(15 mg–1,5000 mg);

Bilberry (standardized to 25% anthocyanosides) is rich in the bio-flavonoid complex anthocyanosides. These active constituents support visual adaptation to light and also help maintain normal nighttime vision. Anthocyanosides support the health of the eye and circulatory system by providing antioxidant activity, improving microcirculation, and supporting healthy connective tissue formation (160 mg)(16 mg–1,600 mg);

Taurine is an amino acid used as a building block of all the other amino acids; it is found in the eye, heart muscle, white blood cells, skeletal muscle, and central nervous system (900 mg)(90 mg–9,000 mg);

Lutein and zeaxanthin Extract are powerful antioxidants believed to protect the body and eyes from damaging free radicals. Lutein is from the carotenoid family and consists of naturally occurring fat-soluble pigments in plants. It is the main carotenoid found in the retina of the eye, and may be effective in the treatment of cataracts. It works extremely well against sunlight damage, and supplementation with 6 mg of Lutein daily may decrease the occurrence of macular degeneration by more than 50%. With no known contraindications, it is a safe, effective, and powerful nutritional support for healthy vision (see 0011);

DHA (Docosahexaenoic Acid) is another nutrient that has become more prominent regarding eye health. This omega-3 fatty acid is found primarily in oily fish such as tuna, mackerel and salmon. A recent New England Journal of Medicine study showed that people who had eaten canned tuna three times a week had an almost miraculous stabilization and sometimes even improvement in their visual acuity and the DHA in the tuna was responsible for this. DHA is critical for retinal health and macular health (500 mg)(10 mg–2,000 mg);

Ginkgo Biloba (120 mg)(10 mg–2,000 mg) and Grape Seed Extract (200 mg)(10 mg–2,000 mg)—Bioflavonoids and herbs, including grape seed extract and gingko biloba act as antioxidants, strengthen and promote healthy collagen.

In addition to the key components, other components are optionally included such as: Thiamin (Vitamin B1), Riboflavin (Vitamin B2), Niacin (Vitamin B3), Pyroxidine HCL (Vitamin B6), Methylcobolamin (Vitamin 12), Biotin, Pantothenic Acid (Vitamin B5), Iodine (kelp), Magnesium, Zinc, Selenium, Copper, Manganese, Chromium, Molybdenum, N-acetyl cysteine, Bioflavenoids (quercetin, rutin, citrus Biocomplex), plant enzymes, L-glycine, L-Glutathione, Baron and Malic Acid.

The following table depicts a preferred formulation:

| | Amount per serving | % daily value |
|---|---|---|
| Vitamin A - (Betatene) (as natural carotenoid beta carotene, alpha carotene, lutein, zeaxanthin, cryptoxanthin and palmitate) | 5,000 IU | 100% |
| Vitamin C - (as calcium ascorbate) | 1 g (1,000 mg) | 1,666% |
| Vitamin D3 (as cholecarciferol) | 700 IU | 175% |
| Natural Vitamin E (as d-alpha tocopherol succinate, gamma, delta and beta) | 500 IU | 1,668% |
| Thiamine(Vitamin B1 HCI) | 50 mg | 3,333% |
| Riboflavin (Vitamin B2) | 10 mg | 588% |
| Niacinamide (Vitamin B3) | 70 mg | 346% |
| Pyridoxine HCL (Vitamin B6) | 50 mg | 2,500% |
| Folic Acid (as folacin) | 800 mcg | 200% |
| Vitamin B12 (Methylcobalamin) | 500 mcg | 8,333% |
| Biotin | 300 mcg | 100% |
| Pantothenic Acid (Vitamin B5 as d-calcium pantothenate) | 50 mg | 500% |
| Iodine (as kelp) | 75 mcg | 51% |
| Magnesium (from 1,053 mg Taurinate) | 84 mg | 21% |
| Magnesium (from oxide and magnesium ascorbate) | 316 mg | 79% |
| Zinc (as L-monomethionine) | 30 mg | 200% |
| Selenium (Selenomethionine) | 200 mcg | 286% |
| Copper (as chelate) (AAC) | 2 mg | 1000% |
| Manganese (as chelate) AAC) | 2 mg | 100% |
| Chromium (as chromium polynicotinate) (Chromemate) | 200 mcg | 166% |
| Molybdenum (as chelate (AAC) | 75 mcg | 100% |
| Bilberry Extract (standardized to 25% Anthocyanosides) | 160 mg | * |
| Lycopene (from 200 mg Lyc-o-Mato) | 10 mg | * |
| Lutein (From 400 mg FloraGLO Extract) | 20 mg | * |
| Zeaxanthin (from 400 mg FloraGlo Extract) | 880 mcg | * |
| Alpha Lipoic Acid | 300 mg | * |
| N-Acetyl-Cysteine | 600 mg | * |
| Bioflavonoid (as quercetin) | 100 mg | * |
| Bioflavonoid (as rutin) | 100 mg | * |
| Bioflavonoid (Citrus BioComplex Standardized to 50%) | 125 mg | * |
| Plant Enzymes (Amylase 2,000 SKB Cellulase 25 CU, Protease 7,500 HUT, Lipase 25 FIP and Lactase 250 ALLLU) | 50 mg | * |
| Black Pepper (piper nigrum) (fruit extract) (Bioperine) | 5 mg | * |
| L-Glycine | 100 mg | * |
| L-Glutathione | 10 mg | * |
| L-Taurinate (from magnesium taurinate) | 900 mg | * |
| DHA (Docosahexaenoic Acid) | 500 mg | * |
| EPA | 300 mg | * |
| Gingko Biloba | 120 mg | * |
| Grape Seed Extract | 200 mg | * |

*Daily Value Not Established
Other Ingredients: Magnesium Stearate, Silica and Kosher Gelatin (capsule)
Please Note:
1,000 mcg (microgram) = 1 mg (milligram)
1,000 mg = 1 g (gram)

Although the invention has been described primarily in connection with special and preferred embodiments, it will be understood that it is capable of modification without departing from the scope of the invention. The following claims are intended to cover all variations, uses, or adaptations of the of the invention, following, in general the principles thereof and including such departures from the present disclosure as come within known or customary practice in the field to which the invention pertains, or as are obvious to persons skilled in the field.

What is claimed is:

1. An eyesight enhancement and maintenance composition comprising an effective amount of:

Vitamin A;
   Vitamin C;
   Vitamin E;
   Gingko Biloba;
   Docosahexanoic Acid;
   Alpha Lipoic Acid;
   Bilberry Extract;
   Selenium;
   L-Taurine;
   Lutein Extract;
   Lycopene; and
   Grape Seed Extract.

2. An eyesight enhancement and maintenance composition comprising:

10–2000 mg Gingko Biloba;
   10–2000 mg Docosahexanoic Acids;
   10–15000 mg Vitamin C;
   50–5000 IU Vitamin E;
   16–1600 mg Bilberry Extract;
   100 mcg–1000 mg Lutein Extract;
   90–9000 mg L-Taurine
   10–2000 mg Grape Seed Extract
   50–600 mg Selenium
   50–1000 mg Alpha Lipoic Acid; and
   6–100 mg Lycopene.

* * * * *